US 6,632,837 B1

(12) United States Patent
Avram

(10) Patent No.: US 6,632,837 B1
(45) Date of Patent: Oct. 14, 2003

(54) COMPOSITIONS CONTAINING A SELENIUM MONOBROMIDE-OIL REACTION PRODUCT AND EPICHLOROHYDRIN AND METHODS OF MAKING THE SAME

(76) Inventor: Elena Avram, 545 W. End Ave., Apt. 8E, New York, NY (US) 10024

( * ) Notice: Subject to any disclaimer, the term of this patent is extended or adjusted under 35 U.S.C. 154(b) by 0 days.

(21) Appl. No.: 10/274,151

(22) Filed: Oct. 21, 2002

(51) Int. Cl.[7] .............. A61K 31/20; C07F 7/02
(52) U.S. Cl. .......... 514/558; 554/77; 424/702; 514/475
(58) Field of Search .............. 514/558, 475; 554/77; 424/702

(56) References Cited

U.S. PATENT DOCUMENTS

| 4,368,206 A | 1/1983 | Revici .......... 424/312 |
| 4,416,869 A | 11/1983 | Revici .......... 424/164 |
| 4,564,634 A | * 1/1986 | Revici .......... 514/558 |
| 4,565,690 A | 1/1986 | Revici .......... 424/10 |
| 4,609,552 A | 9/1986 | Revici .......... 424/164 |
| 4,663,165 A | 5/1987 | Revici .......... 424/131 |
| 4,681,753 A | 7/1987 | Revici .......... 424/10 |
| 4,851,437 A | 7/1989 | Revici .......... 514/529 |

OTHER PUBLICATIONS

Revici, Emanuel, Research in Physiopathology as Basis of Guided Chemotherapy *With Special Application to Cancer*, 512–518 (D. Van Nostrand Company, Inc.) (1961).

* cited by examiner

*Primary Examiner*—Frederick Krass
(74) *Attorney, Agent, or Firm*—Winston & Strawn

(57) ABSTRACT

A composition of selenium monobromide-oil reaction product including a reaction product of selenium momobromide-in-oil prepared from eleostearic acid and selenium monobromide, which contains at least about 0.1 percent of selenium monobromide and exhibits ultraviolet absorption maxima typical of conjugated trienes and conjugated dienes and pharmnaceutical composition thereof for administration to a subject in a therapeutically effective amount to treat neoplastic conditions such as cancer. Methods of making such compositions are also encompassed, as are methods for treating neoplastic conditions by administering to a subject an effective amount of a selenium monobromide-oil reaction product with epichlorohydrin.

20 Claims, No Drawings

COMPOSITIONS CONTAINING A SELENIUM MONOBROMIDE-OIL REACTION PRODUCT AND EPICHLOROHYDRIN AND METHODS OF MAKING THE SAME

FIELD OF INVENTION

The invention relates to compositions of selenium monobromide-oil reaction product and further relates to pharmaceutical compositions containing these reaction products. Methods of making and using such compositions for treating the symptoms of neoplastic conditions are also encompassed.

BACKGROUND ART

The antitumoral and antineoplastic activity of selenium derivatives has already been described in earlier patents. For example, U.S. Pat. No. 4,564,634 discloses compositions of selenium incorporated in tung oil, while U.S. Pat. No. 4,681,753 discloses compositions of certain dialkyl diselenides and ketones.

These compositions are effective for the treatment of certain neoplastic conditions, but I have found that pharmaceutical compositions containing a selenium monobromide-oil reaction product in combination and preferably with epichlorohydrin provide improved performance and are effective in treating a wide range of neoplastic conditions.

SUMMARY OF THE INVENTION

The invention relates to a composition of selenium monobromide-oil reaction product useful in treating a subject suffering from neoplastic conditions. The selenium monobromide-oil reaction product typically exhibits ultraviolet absorption maxima typical of conjugated trienes and conjugated dienes. The reaction product comprises of selenium monobromide-in-oil which contains at least about 0.1 weight percent of selenium monobromide, prepared from an oil containing eleostearic acid and selenium monobromide.

Pharmaceutical compositions containing these reaction products and a pharmaceutically acceptable carrier are also encompassed by the invention A process of preparing a selenium monobromide-oil reaction product is another embodiment of the invention. The process comprises reacting sufficient amounts of an eleostearic acid containing oil and selenium monobromide at a sufficient temperature and for a sufficient time to incorporate at least about 0.1 weight percent of selenium monobromide in the oil. The process generally involves reacting about 50 to 150 parts of oil with about 1 to 10 parts of powdered selenium monobromide at a temperature of 200 to 250° C. for a period of about 1 to 4 hours, until the reaction product becomes substantially clear, continuing heating the reaction product for about an additional 15 minutes to an hour, and decanting off the selenium monobromide which has not reacted.

A further embodiment is a method of treating a subject affected with a neoplastic condition, such as cancer. The method usually involves administering a therapeutically effective amount of a pharmaceutical composition containing a selenium monobromide-oil reaction product. The pharmaceutical composition is typically administered to the subject 2 to 4 times daily in capsule form, although a combination between oral and intradermal administration is also often used.

DETAILED DESCRIPTION OF THE PREFERRED EMBODIMENTS

The present invention relates to compositions of selenium monobromide-oil reaction product that exhibits a substantial antineoplastic activity. More specifically the invention encompasses compositions comprising a reaction product of selenium momobromide-in-oil prepared from oil containing eleostearic acid and selenium monobromide. The reaction product generally contains at least about 0.1 weight percent selenium monobromide and preferably between about 0.1 to 5 weight percent. Typically the reaction product exhibits ultraviolet absorption maxima associated with conjugated trienes and conjugated dienes.

Generally, any oil containing eleostearic acid can be used. Most preferably, however, the oils containing eleostearic acid in the form of 9, 11, 13-octadecatrienoic acid of formula $CH_3-(CH_2)_3-CH=CH-CH=CH-CH=CH-(CH_2)_7-COOH$ are preferred.

This acid is a fatty acid and is the chief component in "tung oil." By warming selenium monobromide with oil containing eleostearic acid at a temperature of about 200 to 250° C., a selenium monobromide reaction product is formed.

Typically, the percentage of selenium monobromide in compositions prepared in this manner may vary within a broad range, but is preferably between about 0.1 to 5 weight percent for therapeutical use, compounds containing between about 2 to 4 weight percent by weight of selenium monobromide-oil reaction product are particularly useful.

The invention further relates to pharmaceutical compositions for administration to a human subject suffering from a neoplastic condition such as cancer. The pharmaceutical compositions typically include a reaction product of selenium momobromide-in-oil prepared from eleostearic acid and selenium monobromide, and a pharmaceutically acceptable carrier. Advantageously the pharmaceutical composition generally contains at least 0.1 weight percent. Preferably, however, the composition comprises about 0.1 to 5 weight percent of selenium monobromide-oil reaction product, more preferably about 2 to 4 weight percent and most preferably about 3 weight percent. The balance of the composition is usually composed of a pharmaceutically acceptable carrier. A liquid such as an oil, water or saline solution is typically used. If an oil is used as a carrier, vegetable, animal, fish oil, tung oil, sesame oil or combinations thereof can be used. Preferred oils are tung and sesame oils and combinations thereof.

The pharmaceutical composition usually further includes epichlorohydrin to enhance the antineoplastic properties of the reaction product. Epichlorohydrin is often included in an amount of between about 0.1 and 5 weight percent of the composition and more preferably between 0.5 and 1 weight percent. The epichlorohydrin used is preferably hydrolyzed.

Besides epichlorohydrin other epoxy agents can be used together or as an alternative to enhance the antineoplastic properties of the reaction product. Examples include epibromohydrine, 1,2-epoxy butane, 1,2-epoxy, 3 allyloxypropane, epoxyoctoxypropane, and 2,3-epoxypropylacrylate.

The pharmaceutical composition is usually sterilized by heating.

Generally the pharmaceutical composition is prepared as a single dosage form wherein the selenium monobromide-oil reaction product is present in an amount of from about 0.1 ml to 200 ml and more preferably about 05. to 5 ml per unit.

Advantageously, a epichlorohydrin solution is present in an amount of from about 0.1 ml to 50 ml and more preferably about 1 to 5 ml per unit.

A further embodiment of the invention relates to a process of preparing a selenium monobromide-oil reaction product from eleostearic acid containing oil and selenium monobromide. The process typically comprises reacting sufficient amounts of an eleostearic acid containing oil and selenium monobromide at a sufficient temperature and for a sufficient time to incorporate at least about 0.1% of selenium monobromide in the oil.

A preferred embodiment of the inventive process consists of warming selenium monobromide with an oil, preferably a combination of sesame and "tung oil" up to a point when the mixture becomes clear, so that the elementary selenium monobromide substantially disappears. This process typically consists of reacting 50 to 150 parts, more preferably 75 to 125 parts and most preferably 97 parts oil containing eleostearic acid with 1 to 10 parts, more preferably 2 to 5 parts and most preferably 3 parts of powdered selenium monobromide at a temperature of about 200 to 250° C. for a period of about 1 to 4 hours and most preferably about 2 to 3 hours, until the reaction product becomes substantially clear. This is followed by continuing to heat the reaction product for about an additional 15 minutes to hour and most preferably for about a half hour, followed by decanting off the selenium monobromide that has not reacted.

During heating, the mixture is typically oxidized or heated in the presence of oxygen. The oxygen can be obtained by merely heating the formulation open to the atmosphere but preferably and advantageously, the source of oxygen is an oxygen-containing gas, such as air, injected into or bubbled through a heated oil, such as sesame oil/tung oil, according to the invention. The injected gas also serves as a source of agitation to facilitate the oxidation of the oil.

Typically the oil used in this process is a reaction product of an animal, vegetable, or fish oil, or tung oil or sesame oil, or a combination thereof. More preferably tung oil or sesame oil and most preferably a combination of sesame and tung oil are used.

Advantageously, about 0.1 to 5 parts, more preferably 0.5 to 1 part epichlorohydrin can be added to the selenium monobromide-oil reaction product to further enhance its antineoplastic properties.

The epichlorohydrin used is preferably hydrolyzed. The hydrolyzed epichlorohydrin is prepared by heating the epichlorohydrin in water to provide the aqueous solution of epichlorohydrin; and the method further comprises combining a therapeutically effective amount of selenium monobromide-oil reaction product with the epichlorohydrin solution.

A further embodiment of the invention relates to a method of treating a subject affected with a neoplastic condition, such as cancers, sarcomas, lymphomas and leukemias. The method generally comprises the step of administering a therapeutically effective amount of a pharmaceutical composition containing a selenium monobromide-oil reaction product at least once daily or more preferably 2 to 4 times daily, depending on the dosage amount and form of administration, until disappearance of the neoplastic condition.

The magnitude of a prophylactic or therapeutic dose of the selenium monobromide-oil reaction product use in the treatment of a subject affected by neoplastic conditions, will vary with the severity of the condition to be treated and the route of administration. The dose, and perhaps the dose frequency, will also vary according to the age, body weight, and response of the individual patient.

In general, the total daily dose range, for the conditions described herein, is typically from about 0.1 ml to about 500 ml administered in single or divided doses orally, by injection, topically, transdermally, or locally by inhalation. Preferred administration routes include the oral and injection routes or a combination of the two. For example, a typical oral daily dose range should be from about 0.1 ml to 200 ml, preferably about 1 ml to 100 ml, and more preferably about 2 ml to 50 ml of the active components (i.e., excluding excipients and carriers).

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know how and when to interrupt, adjust, or terminate therapy in conjunction with individual patient response.

The product of the invention have in general a low toxicity, which permits their use in adequately high amounts to treat neoplastic conditions. Good clinical results have been obtained as indicated in the examples below.

Although any suitable route of administration may be employed for providing the patient with an effective dosage of the composition according to the methods of the present invention, preferred routes include, for example, oral and injection, and like forms of administration may be employed. "Injection" typically includes parenteral, intravenous, subcutaneous, and intramuscular routes. Suitable dosage forms include tablets, troches, dispersions, suspensions, solutions, capsules, gel-caps, patches, one-shot injections, needleless injectors, and the like, although oral and injectable dosage forms are preferred. A preferred injection route is intramuscularly.

The pharmaceutical compositions used in the methods of the present invention include the active ingredients described above, and may also contain pharmaceutically acceptable carriers, excipients and the like, and optionally, other therapeutic ingredients. The active ingredients used in the methods and compositions can be administered individually, as a single composition that contains all the ingredients, or in any combination thereof.

The compositions for use in the methods of the present invention may be prepared in various formulations, such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets), with the oral capsules and oral liquid preparations being preferred. The most preferred oral solid preparations are capsules.

Because of their ease of administration, capsules represent the most advantageous oral dosage unit form. A capsule may be prepared with one or more accessory ingredients for example epichlorohydrin. Capsules my be prepared by manual or mechanical means with a suitable machine. Desirably, in one embodiment each unit dose, e.g., capsule, contains from about 0.1 mg to 1,000 mg of the active ingredient, preferably about 0.5 mg to 100 mg, and more preferably about 1 mg to 50 mg of the selenium monobromide-oil reaction mixture.

In addition to the common dosage forms set out above, the compounds of the invention can also be administered by controlled-release means or delivery devices that are well known to those of ordinary skill in the art, such as those described in U.S. Pat. Nos.: 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, the disclosures of which are incorporated herein by reference. Preferred controlled-release means are disclosed by: U.S. Pat. Nos. 5,427,798 and 5,486,362; WO 9404138; CA 1239034; and European Patent Application Nos. 467488 and 171457, all of which are incorporated herein by reference. These dosage forms can be used to provide slow or controlled-release of one or more of the active ingredients therein using, for example, hydroxypropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for oral administration, such as tablets, capsules, gelcaps, and caplets, that are adapted for controlled-release are encompassed by the present invention.

The compositions of the invention is used to treat patients with different neoplastic conditions, and might sometimes alleviate some of the symptoms of the condition without necessarily eliminating the disease itself. In application, however, both subjective and objective improvements have been found to be beneficial to the subjects treated with these compositions and are encompassed by the invention.

EXAMPLES

The following examples illustrate the method of treating patients with neoplastic conditions according to the invention without, however, limiting the invention in any way.

The medicament to be administered is a selenium monobromide and sesame/tung oil reaction product that has incorporated therein about 3 weight percent selenium monobromide. This medicament is conveniently provided in gelatin capsules for administration. For example, 20 drops of the reaction product can be placed in 00 capsules. Greater amounts can be provided in larger capsules or can be administered as a drinkable liquid.

In the following examples, 770 g of sesame oil and 200 g of tung oil were mixed with 30 g powdered selenium monobromide. The mixture was heated to about 225° C. for 2 to 3 hours until the reaction mixture was clear. During heating the mixture was oxygenated to facilitate the reaction. After the mixture was substantially clear, the mixture was further heated for about half an hour. After heating, the non-reacted selenium monobromide was decanted off and 0.5 g of hydrolyzed epichlorohydrin was added to the reaction product to produce the selenium monobromide-oil reaction product (Secol) used in the following examples.

Case 1

Subject, White Female, 24 Years of Age

Prior to consultation, the subject was diagnosed with anorexia and slightly damaged liver. She stopped menstruating at that time and noticed the onset of the growth of a small amount of facial hair and hair loss on her head. She began to menstruate again, but grew additional facial hair. She was treated by an endocrinologist and diagnosed as having a hormonal imbalance. She was treated by a physician practicing holistic medicine with enzymes, vitamins and live cells injections.

After which she was observed as having a swelling in the left eye. An ophthalmologist consulted noted eye proptosis vision in the left eye and a malignancy had developed in the left nasal passage and proceeded into the left eye and spread through the cranium and became an enlarged tumor of the head. Treatment was begun with selenium monobromide-oil reaction product (Secol) 10 drops orally, four times per day. Observation over a period of three months indicated an improved condition. The tumor near the mouth disappeared and no symptoms were noted except for multiple allergies.

Treatment was continued with Secol, 50 drops orally, four times per day. Vision returned to the left eye, which previously had exhibited no vision. She was able to breath through her nostrils, which previously could not be done. The subject exhibited no manifestations of pathology as observed by CAT-scan, X-ray and blood analysis.

Case 2

Subject, Female, 73 Years of Age

Colonic biopsy revealed ulcerated infiltrating colonic adenocarcinoma with adjacent mucosal hyperplasia. A total fiberoptic colonoscopy was performed and revealed the presence of restricting annular nodular fibrous lesions at 40 cm. CAT-scan of the abdomen and pelvis showed uterine enlargement, irregularity in contour with narrowing of the lumen of a loop of the bowel in the abdomen.

Surgery was planned for the carcinoma. Prior to the surgery, the subject was treated with 15 drops of Secol, four times per day. Within three months, the subject exhibited regular bowel movements, no bloat and relative freedom from symptoms. She experienced only minimal rectal bleeding.

The treatment was continued and at the end of one year, symptoms had disappeared and no pathology was observed by examination. The contemplated surgery was not required.

Case 3

Subject, Female 52 Years of Age

Diagnosed with breast cancer she had had a mastectomy of the left breast. The cancer returned in the right breast.

Treatment was begun with Secol 20 drops in a 00 capsule form, four times per day and 3 cc once per day intramuscularly. One month later, lesions were paler and flatter. No further pain or other sensation was observed.

Three cc once per day intramuscularly was continued. The subject responded quite well, lesions almost disappeared completely. No further lesions were found and the subject as of approximately one year after the initiation of treatment continued with capsule treatment, four times per day.

Case 4

Subject, Male, 81 Years of Age

Initially diagnosed with lung cancer, CAT-scan showed multiple large tumors in the mediastinum and smaller ones in both lungs. The subject had a history of hypertension for 10 years. Both lung fields showed a faintly nodular type of pattern in the marking and in the left lung, there were irregular infiltrates.

The subject began treatment with Secol 10 drops, four times a day. After two months, the subject began to feel better and exhibited no further coughing. After being seen on a regular basis for one year, X-rays indicated improvement in the condition. The subject exhibited much greater breathing capacity and was able to walk again which he had been unable to do previously because of the lung condition.

Case 5
Subject, White Female, 61 Years of Age

Subject had a history of gross hematury, had been treated for a urinary tract infection. After persistent bleeding, cystoscopic analysis led to a diagnosis of bladder carcinoma.

The subject had surgery for bladder cancer on three separate occasions. The continuing severe bleeding and sensitivity in the lower abdomen continued to be a symptom and indications by X-ray showed that the cancer had spread.

Thereafter, the subject began treatment with 00 Secol capsules, four times per day. One year later, the subject was relatively symptom-free without additional lesions as determined by X-rays, CAT-scan and blood analysis.

Case 6
Subject, Male, Middle-aged

Initial diagnosis was malignant lymphoma. The diagnosis was confirmed at another hospital after a biopsy of the left inguinal lymph node. CAT-scan of the chest demonstrated extensive adenopathy with a possible hilar mass. A lymphaniogram showed a few filling defects in several of the para-aortic lymph nodes.

The subject underwent treatment with a combination of conventional cytotoxic chemotherapy. A CAT-scan showed a complete regression of the extensive mediastinal nodes and hilar lymphadenopathy. Follow-up CAT-scan demonstrated extensive hilar and mediastinal adenopathy as well as a multiplicity of pulmonary nodules in both lungs.

Thereafter, the subject began treatment with 00 Secol capsules, with two capsules being administered four times per day (a total of eight capsules per day). A CAT-scan fourteen months later revealed regression of the lymph nodes and disappearance of some. The subject became symptom-free and was able to work again.

Case 7
Subject, White Female, 47 Years of Age

The subject was initially diagnosed with breast carcinoma. The subject's medical history showed a thymus irradiation at the age of 6 months because of enlargement. Also, radiation treatments had been given for enlarged tonsils and poison ivy. At 12 years of age, the subject had the first of two radical thyroid operations. As an adult, the subject had a radical mastectomy of the right breast for multifocal intraductal adenocarcinoma.

Approximately, seven years thereafter, a biopsy of the sternum revealed adenocarcinoma of the breast and lung lesions. A bone scan revealed a small spot on the left side of T-12 spine.

Thereafter, the subject began treatment with Secol 10 drops, four times per day. Her condition improved and one year later she was relatively symptom-free with less pain in the chest. X-ray examination revealed that the lung lesions were no longer visible.

Case 8
Subject, Male, 60 Years of Age

Initially diagnosed for glioblastoma multiformed (in the brain), the tumor was characterized by moderate nuclear pleomorphism with a variety of astrocytic forms including gemistocytic astrocytes. The subject underwent surgery after which X-ray showed that cancer cells were still present.

Thereafter, the subject began treatment with a 00 Secol capsule administered four times per day. One year after the beginning of this treatment, the subject was relatively symptom free, speaking better, had increased strength, less pain and was responding well to medication. Memory improvement was also reported.

The term "about," as used herein, should generally be understood to refer to both numbers in a range of numerals. Moreover, all numerical ranges herein should be understood to include each whole integer within the range.

Although preferred embodiments of the invention have been described in the foregoing Detailed Description, it will be understood that the invention is not limited to the embodiments disclosed, but is capable of numerous rearrangements and modifications of parts and elements without departing from the spirit of the invention. It will be understood that the chemical details of every design may be slightly different or modified by one of ordinary skill in the art without departing from the teachings of the present invention.

What is claimed is:

1. A composition comprising a reaction product prepared from an oil containing eleostearic acid, and selenium monobromide, which comprises at least about 0.1 weight percent of reacted selenium monobromide and exhibits ultraviolet absorption maxima typical of conjugated trienes and conjugated dienes.

2. The composition according to claim 1 wherein the selenium monobromide content of the reaction product is about 2 to 3 weight percent.

3. The composition of claim 1, wherein the oil is an animal, vegetable, fish oil, tung oil, sesame oil or a combination thereof.

4. The composition of claim 1, wherein the composition contains a combination of tung and sesame oils.

5. The composition of claim 1, further comprising an epichlorohydrin solution, wherein the epichlorohydrin is optionally hydrolyzed.

6. The composition of claim 5, wherein the epichlorohydrin solution is present in an amount of between about 0.1 and 5 weight percent of the composition.

7. The composition of claim 6, comprising about 3 weight percent reacted selenium monobromide and about 0.5 to 1 weight percent hydrolyzed epichlorohydrin in about 70 to 80 weight percent sesame seed oil and about 16 to 26.5 weight percent tung oil, with the amounts adding to 100% in the composition.

8. A process of preparing a reaction product which comprises reacting an eleostearic acid-containing oil and selenium monobromide at a sufficient temperature and for a sufficient time to incorporate at least about 0.1 weight percent of selenium monobromide in the oil.

9. The process of claim 8, wherein about 50 to 150 parts of oil are reacted with about 1 to 10 parts of powdered selenium monobromide at a temperature of 200 to 250° C. for a period of about 1 to 4 hours, until the reaction product is formed.

10. The process of claim 8, wherein a clear reaction product is formed and is recovered by separation from unreacted selenium monobromide.

11. The process of claim 8, wherein the oil is an animal, vegetable, fish oil, tung oil, sesame oil, or a combination thereof.

12. The process of claim 8, further comprising mixing the selenium monobromide-oil reaction product with about 0.1 to 5 parts epichlorohydrin, wherein the epichlorohydrin is optionally hydrolyzed.

13. The process of claim 12, wherein the hydrolyzed epichlorohydrin is prepared by heating the epichlorohydrin in water to provide an aqueous solution of epichlorohydrin; and the method further comprises combining a therapeutically effective amount of selenium monobromide-oil reaction product with the epichlorohydrin solution.

14. A method of treating a subject affected with a neoplastic condition comprising the following steps: administering a therapeutically effective amount of a composition according to claim 1 to a subject at least once daily until disappearance of the neoplastic condition.

15. The method of claim 14, wherein the composition is administered to the subject 2 to 4 times daily by oral or intradermal administration or a combination.

16. The method of claim 14, wherein the administering comprises injection, inhalation, oral administration or intradermal administration.

17. The method of claim 14, wherein the composition is administered with epichlorohydrin in an amount of between about 0.1 and 5 weight percent of the composition, wherein the epichlorohydrin is optionally hydrolyzed.

18. A pharmaceutical composition for administration to a human subject comprising: a reaction product prepared from an oil containing eleostearic acid, and selenium monobromide, which contains at least 0.1 weight percent of reacted selenium monobromide and exhibits ultraviolet absorption maxima typical of conjugated trienes and conjugated dienes and a pharmaceutically acceptable liquid which acts as a carrier.

19. The composition of claim 18, in single dosage form wherein the selenium monobromide-oil reaction product is present in an amount of about 3 weight percent and further comprising epichlorohydrin.

20. The composition of claim 18, in single dosage form wherein the selenium monobromide-oil reaction product is present in an amount of about 1 to 100 ml per unit and further comprising an epichlorohydrin solution present in an amount of from about 0.01 ml to 5 ml.

* * * * *

UNITED STATES PATENT AND TRADEMARK OFFICE
CERTIFICATE OF CORRECTION

| | | |
|---|---|---|
| PATENT NO. | : 6,632,837 B1 | Page 1 of 1 |
| DATED | : October 14, 2003 | |
| INVENTOR(S) | : Avram | |

It is certified that error appears in the above-identified patent and that said Letters Patent is hereby corrected as shown below:

<u>Title page,</u>
Item [57], ABSTRACT,
Line 7, change "pharmnaceutical" to -- pharmaceutical --.

<u>Column 2,</u>
Line 67, change "05. to 5 ml per unit." to -- 0.5 to 5 ml per unit. --.

<u>Column 8,</u>
Line 22, after "wherein the" insert -- reacted --.

Signed and Sealed this

Ninth Day of December, 2003

JAMES E. ROGAN
*Director of the United States Patent and Trademark Office*